(12) United States Patent
Schmidt et al.

(10) Patent No.: US 7,063,662 B2
(45) Date of Patent: Jun. 20, 2006

(54) SUPPLY UNIT FOR ACCOMMODATING MEDICAL INSTRUMENTS

(75) Inventors: Hartmut Schmidt, Heilshoop (DE); Günter Olbrich, Lübeck (DE)

(73) Assignee: Dräger Medical AG & Co. KGaA, Lübeck (DE)

( * ) Notice: Subject to any disclaimer, the term of this patent is extended or adjusted under 35 U.S.C. 154(b) by 266 days.

(21) Appl. No.: 10/691,995

(22) Filed: Oct. 23, 2003

(65) Prior Publication Data

US 2004/0094687 A1 May 20, 2004

(30) Foreign Application Priority Data

Nov. 20, 2002 (DE) ............................. 102 54 294

(51) Int. Cl.
*A61B 1/00* (2006.01)
(52) U.S. Cl. .................. 600/132; 606/1; 137/357; 248/637
(58) Field of Classification Search ................ 600/132; 248/129, 343, 637; 137/355, 17, 343, 356, 137/597, 357; 604/259; 606/1
See application file for complete search history.

(56) References Cited

U.S. PATENT DOCUMENTS

| | | | | |
|---|---|---|---|---|
| 4,402,313 A | * | 9/1983 | Yabe | .......................... 600/132 |
| 4,654,493 A | * | 3/1987 | Drager et al. | ............. 200/302.1 |
| 4,708,126 A | * | 11/1987 | Toda et al. | ................... 600/132 |
| 4,883,558 A | * | 11/1989 | Bellis et al. | ................. 156/292 |
| 5,113,897 A | * | 5/1992 | Kummerfeld et al. | ....... 137/357 |
| 6,213,481 B1 | | 4/2001 | Marchese et al. | |
| 6,617,845 B1 | * | 9/2003 | Shafiyan-Rad et al. | 324/207.16 |
| 2003/0197100 A1 | | 10/2003 | Marchese | |
| 2004/0171913 A1 | * | 9/2004 | Saruya | ....................... 600/132 |

FOREIGN PATENT DOCUMENTS

| | | |
|---|---|---|
| DE | 298 05 019 | 6/1998 |
| DE | 198 08 267 | 9/1999 |
| EP | 0 943 306 | 9/1999 |

\* cited by examiner

*Primary Examiner*—Michael Peffley
*Assistant Examiner*—Alex Toy
(74) *Attorney, Agent, or Firm*—McGlew & Tuttle, P.C

(57) ABSTRACT

The present invention pertains to a supply unit for accommodating medical instruments. A middle part, which is located at an instrument (12) and is equipped with lateral guide surfaces (3), engages a height-adjustable middle part of the supply unit (1) with side cheeks (2) in an accurately fitting manner. So-called end position sensors (4), e.g., photoelectric cells, which send a signal to an evaluating and control unit when the height-adjustable middle part of the supply unit (1) has been moved upward to the extent that pins (14) arranged there are completely accommodated by complementarily designed pin mounts (15) at the middle part of the instrument (12), are provided at the middle part of the supply unit (1). The evaluating and control unit now releases a plug-type connection for the power supply (6, 7), for the data transmission (8, 9) and for the pneumatic supply (10, 11).

18 Claims, 2 Drawing Sheets t1.

t2.

t3.

t4.

t5.

t6.

SUPPLY UNIT FOR ACCOMMODATING MEDICAL INSTRUMENTS

FIELD OF THE INVENTION

The present invention pertains to a supply unit for accommodating medical instruments with a height-adjustable middle part with side cheeks, which are designed for engaging a middle part of a medical instrument with lateral guide surfaces, which are complementary to the side cheeks.

BACKGROUND OF THE INVENTION

It has been known that medical instruments, which are located, e.g., on instrument carriers of traveling and height-adjustable cart systems, can be connected to ceiling-mounted supply units. A mechanical coupling of the instrument to the ceiling-mounted supply unit is brought about via an interface, and the instrument is supplied with electricity and the necessary gases via the ceiling-mounted supply unit.

DE 40 21 013 C2 describes a supply unit with a height-adjustable, vertically oriented connection head, with which a medical instrument can be coupled. A coupling part, which is located at the instrument and is provided with vertical guide surfaces, engages a mounting part present at the connection head in an accurately fitting manner. In the case of an accurately fitting engagement, the electric switching contacts are released such that a suitable height adjustment as well as the setting up of the supply lines to the instrument with the operating media, e.g., electricity and gases, can be performed.

The fact that it is necessary for the user to perform the corresponding setting of the height and to set up the supply lines between the supply unit and the instrument manually, e.g., by plugging in cable and tube connections, in addition to the mechanical coupling operation, proved to be a drawback of the known invention.

SUMMARY OF THE INVENTION

The object of the present invention is therefore to provide a supply unit for accommodating medical instruments, which guarantees an extensive automation during the coupling of the instrument with the supply unit as well as the release of supply lines.

According to the invention, a supply unit for accommodating medical instruments has a height-adjustable middle part with side cheeks, which are designed to engage a middle part of a medical instrument with complementary lateral guide surfaces. So-called end position sensors are provided at the middle part of the supply unit. The sensors send a corresponding signal to an evaluating and control unit connected to the supply unit when the height-adjustable middle part of the supply unit has been moved upward to the extent that pins, which are arranged at the middle part of the supply unit and project upward, are completely accommodated by downwardly open pin mounts at the middle part of the medical instrument. Plug-type connections for power supply, for data transmission and for pneumatic supply are released by the evaluating and control unit in this case. End position sensors means detect that a corresponding signal is, indeed, sent to the evaluating and control unit only when the upwardly projecting pins have reached their end positions in the downwardly open pin mounts.

In a preferred embodiment of the supply unit for accommodating medical instruments, provisions are made for the transfer of medical gases as well as for the generation of a vacuum in the case of the pneumatic supply.

The end position sensors of the supply unit are advantageously designed as photoelectric cells.

In another preferred embodiment of the supply unit, flaps are provided as splash-proofing for the connection jacks for the power supply, for the data transmission as well as for the pneumatic supply.

According to another important embodiment of the supply unit, the supply unit is designed as a ceiling-mounted supply unit.

An exemplary embodiment of the present invention will be shown oh the basis of schematic drawings and explained in greater detail below. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which the preferred embodiment of the invention is illustrated.

DESCRIPTION OF THE PREFERRED EMBODIMENT

Figure 1A:
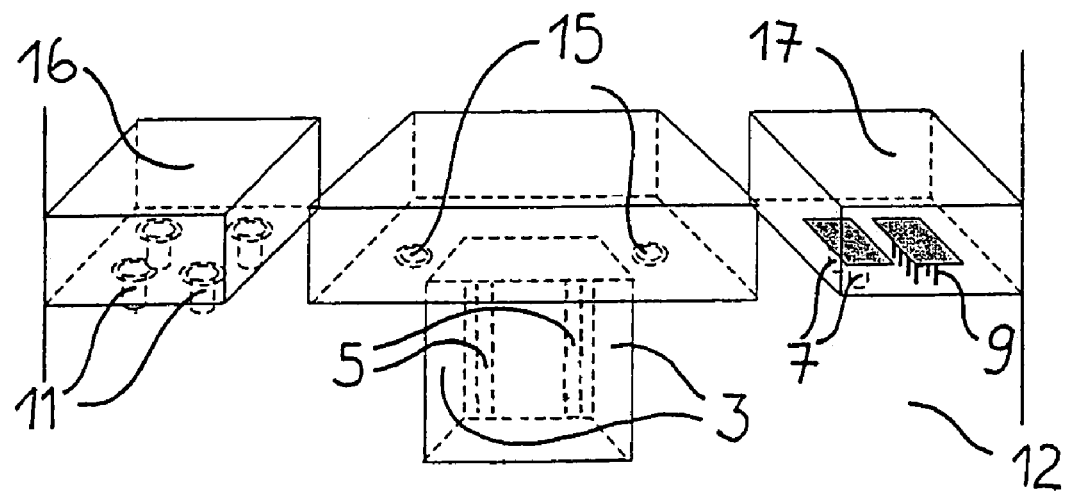
FIG. 1A is a perspective rear view of a medical instrument in the area in which the instrument is accommodated by the supply unit in the top part of the figure.
Figure 1B:
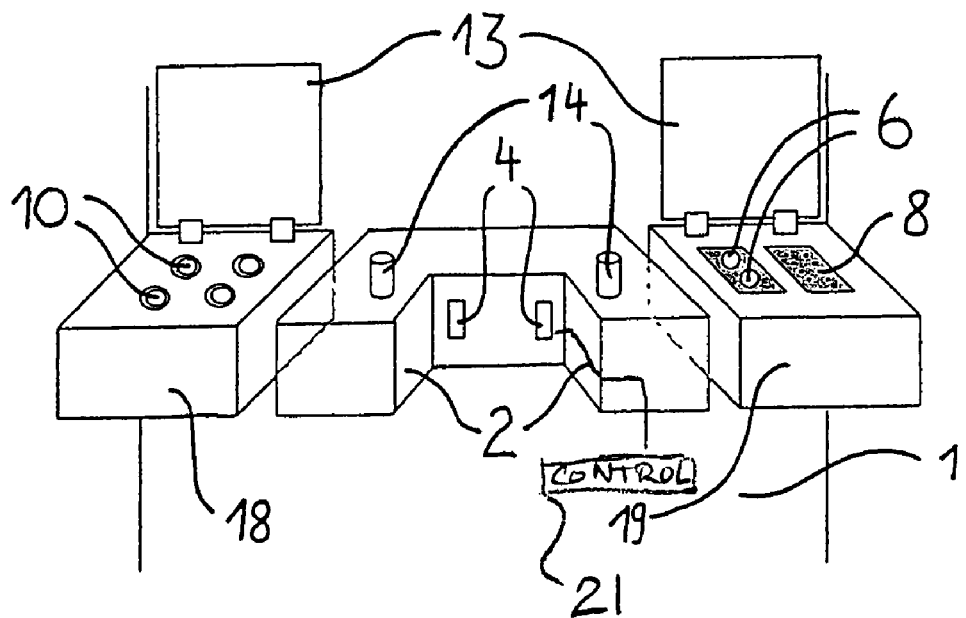
FIG. 1B is a perspective front view of a supply unit, likewise in the area in which the instrument is accommodated by the supply unit in the bottom part of the figure.

Referring to the drawings in particular, FIG. 1A shows a perspective rear view of a medical instrument 12. The instrument 12 is accommodated by the supply unit 1 shown in FIG. 1B. The medical instrument 12 has a middle part in the middle area with lateral guide surfaces 3. On the side of the middle part facing away from the viewer, the middle part has two vertically extending rails 5 shown in dashed line. A first pneumatic coupling part 16 with connection plugs for the pneumatic supply 11 is located on the left at the instrument 12. A first electric and electronic coupling part 17, which has both connection plugs for the power supply 7 and connection plugs for the data transmission 9, is shown on the right-hand side. Furthermore, two pin mounts 15, which are downwardly open, are located in the middle area above the middle part. The bottom part of FIG. 1 shows a perspective front view of a supply unit 1 in the area in which the medical instrument 12 is accommodated by the supply unit 1. On the left; the supply unit 1 has a second pneumatic coupling part 18, which has connection jacks for the pneumatic supply 10, which are complementary to the connection plugs for the pneumatic supply 11. A second electric and electronic coupling part 19 of the supply unit 1, at which both connection jacks for the power supply 6 and connection jacks for data transmission 8 are located, is located on the right. The connection jacks for the power supply 6 are complementary to the connection plugs for the power supply 7, and the connection jacks for the data transmission 8 are complementary to the connection plugs for the data transmission 9.

Side cheeks 2 are designed such that they accurately fit the lateral guide surfaces 3 of the middle part of the medical instrument 12 during coupling. The side cheeks or side surfaces 2 are arranged in the middle area of the supply unit 1. Two end position sensors 4 are arranged on the side of the middle part of the supply unit 1 facing the viewer. The end position sensors 4 send a corresponding signal to an evaluating and control unit 21 in FIG. 1B, when the supply unit 1 has been moved up to the extent that two pins 14 are completely accommodated in the corresponding, complementarily designed pin mounts 15 in the medical instrument 12. The connection jacks for the pneumatic supply 10, for the power supply 6 and for the data transmission 8 can be advantageously covered by flaps 13, which are used as a splash proofing. The flaps 13 are shown in the opened state in the figure. They are opened when the medical instrument 12 is accommodated by the supply unit 1 and they are otherwise closed.

FIGS. 2A to 2F show the time sequence of a coupling as well as uncoupling operation between a medical instrument 12 and a supply unit. 1 designed as a ceiling-mounted supply unit in six lateral views at time t1 through t6.

Figure 2A:
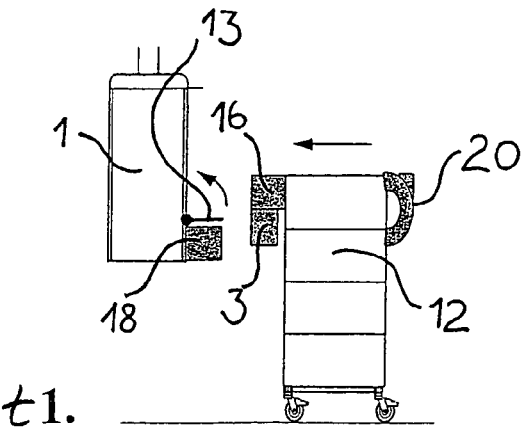
FIG. 2A is a side view of a first part of a time sequence of a coupling operation as well as of an uncoupling operation between a medical instrument and a ceiling-mounted supply unit.

The instrument 12 and the supply unit 1 are still separated in the view at time t1 in FIG. 2A, but the instrument 12 is being moved toward the supply unit 1, indicated by the horizontally extending arrow pointing to the left. The flap 13 designed as a splash proofing for the second pneumatic coupling part 18 of the supply unit 1 is still closed, but it shall be opened for the coupling operation between the instrument 12 and the supply unit 1, represented by the arc-shaped arrow over the flap 3.

The upward movement of the supply unit 1 is initiated from a remote control unit 20 at the instrument 12.

Figure 2B:
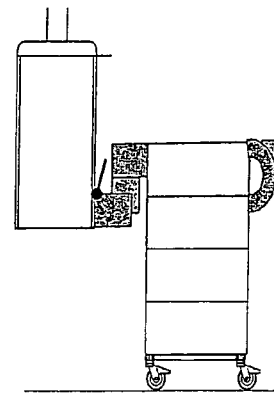
FIG. 2B is a side view of a second part of a time sequence of a coupling operation as well as of an uncoupling operation between a medical instrument and a ceiling-mounted supply unit.

The flap 13 is already shown in the opened position in the view at time t2 in FIG. 2B, and the second pneumatic coupling part 18 of the supply unit 1 as well as the first pneumatic coupling part 16 of the instrument 12 are already arranged one on top of another.

Figure 2C:
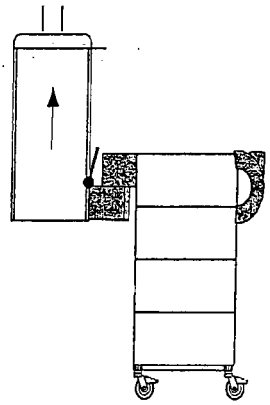
FIG. 2C is a side view of a third part of a time sequence of a coupling operation as well as of an uncoupling operation between a medical instrument and a ceiling-mounted supply unit.

The supply unit 1 has already been moved up in the view at time t3 in FIG. 2C indicated by the vertically extending and upwardly pointing arrow. As a consequence, the instrument 12 no longer has any contact with the floor.

Figure 2D:
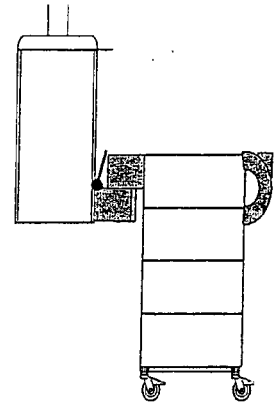
FIG. 2D is a side view of a fourth part of a time sequence of a coupling operation as well as of an uncoupling operation between a medical instrument and a ceiling-mounted supply unit.

The coupled state between the instrument 12 and the supply unit 1 in the resting state is shown in the view at time t4 in FIG. 2D.

Figure 2E:
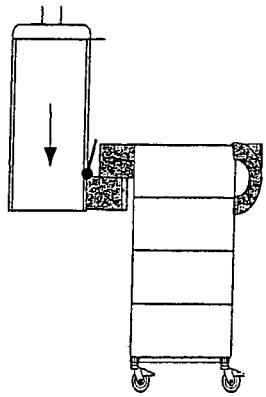
FIG. 2E is a side view of a fifth part of a time sequence of a coupling operation as well as of an uncoupling operation between a medical instrument and a ceiling-mounted supply unit.
Figure 2F:
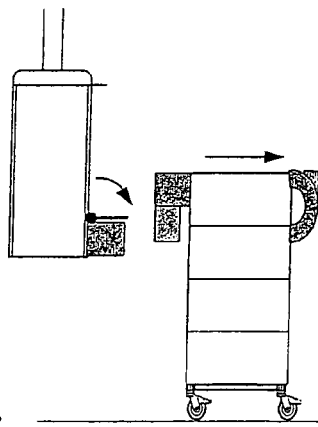
FIG. 2F is a side view of a sixth part of a time sequence of a coupling operation as well as of an uncoupling operation between a medical instrument and a ceiling-mounted supply unit.

The lowering of the supply unit 1 is indicated in the view at time t5 in FIG. 2E by the vertically extending and downwardly pointing arrow.

The supply unit 1 and the instrument 12 are again uncoupled in the view at time t6 in FIG. 2E, and the flap 13 is again closed, recognizable from the rounded arrow extending above it. The horizontally extending arrow pointing to the right shows that the instrument 12 has already been moved away from the supply unit 1.

While a specific embodiment of the invention has been shown and described in detail to illustrate the application of the principles of the invention, it will be understood that the invention may be embodied otherwise without departing from such principles.

What is claimed is:

1. A supply unit for accommodating medical instruments, the supply unit comprising:
   a height-adjustable middle part with side cheeks for engaging a middle part of a medical instrument with lateral guide surfaces which are complementary to the side cheeks;
   pins arranged at the middle part of the supply unit and projecting upwardly;
   a power supply with a plug connection at the middle part of the supply unit;
   a data transmission facility with a plug connection at the middle part of the supply unit;
   a pneumatic supply with a plug connection at the middle part of the supply unit;
   end position sensors provided at the middle part of the supply unit, said end position sensors sending a corresponding signal to an evaluating and control unit when the height-adjustable middle part of the supply unit has been moved upward to the extent that said pins are completely accommodated by complementary and downwardly open pin mounts at the middle part of the medical instrument so that said plug connection for said power supply, said plug connection for said data transmission facility, and said plug connection for said pneumatic supply are released by the evaluating and control unit.

2. A supply unit for accommodating medical instruments in accordance with claim 1, wherein the pneumatic supply provides for the transfer of medical gases as well as the generation of a vacuum.

3. A supply unit in accordance with claim 1, wherein said end position sensors comprise photoelectric cells.

4. A supply unit in accordance with claim 1, wherein said plug connection for said power supply includes power supply connection jacks with flaps as splash proofing for said power supply connection jacks, said connection for said data transmission facility includes transmission connection jacks with flaps as splash proofing for said transmission connection jacks, and said connection for said pneumatic supply includes pneumatic supply connection jacks with flaps as splash proofing for said pneumatic supply connection jacks.

5. A supply unit in accordance with claim 1, wherein the supply unit is ceiling-mounted.

6. A medical instrument supply unit and medical instrument combination comprising:
   a medical instrument with a middle part with lateral guide surfaces and with pin mounts, a power plug/jack connection a data transmission plug/jack connection and a pneumatic plug/jack connection;
   a supply unit with a height stationary part and a height-adjustable middle part with side surfaces for engaging the medical instrument middle part of said medical instrument, the side surfaces being complementary to the lateral guide surfaces of the medical instrument and with pins arranged at the middle part of the supply unit projecting upwardly, a power supply with a power plug/jack connection provided at said height-adjustable middle part, a data transmission facility with a data transmission plug/jack connection provided at said height-adjustable middle part, a pneumatic supply with a pneumatic plug/jack connection provided at said height-adjustable middle part and end position sensors provided at said height-adjustable middle part of the supply unit, said end position sensors sending a corresponding signal to an evaluating and control unit when the height-adjustable middle part of the supply unit has been moved upward to the extent that said pins are completely accommodated by said pin mounts whereby said connection for said power supply, said connection for said data transmission and said connection for said pneumatic supply are in an active state.

7. A combination in accordance with claim 6, wherein the pneumatic supply provides for the transfer of medical gases as well as the generation of a vacuum.

8. A combination in accordance with claim 6, wherein said end position sensors comprise photoelectric cells.

9. A combination in accordance with claim 6, wherein said plug/jack connection for said power supply includes power supply connection jacks with flaps as splash proofing for said power supply connection jacks, said data transmission plug/jack connection for said data transmission facility includes transmission connection jacks with flaps as splash proofing for said transmission connection jacks, and said pneumatic plug/jack connection for said pneumatic supply includes pneumatic supply connection jacks with flaps as splash proofing for said pneumatic supply connection jacks.

10. A combination in accordance with claim 6, wherein the supply unit is ceiling-mounted.

11. A medical instrument supply unit and medical instrument combination comprising:
a medical instrument with a middle part with lateral guide surfaces and with a lower surface having pin mounts and an adjacent lower surface power plug/socket connection facility, an adjacent lower surface data transmission plug/socket connection facility and an adjacent lower surface pneumatic plug/socket connection facility;
a supply unit comprising a power supply, a data transmission facility, a pneumatic supply, a ceiling suspended part and a height-adjustable middle part connected to said ceiling suspended part and adjustably movable relative to the ceiling suspended part, said middle part having side surfaces for engaging the medical instrument middle part of the medical instrument, the side surfaces being complementary to the lateral guide surfaces of the medical instrument middle part, said supply unit middle part having an upper surface with support pins projecting upwardly for mating with said pin mounts, said supply unit having an upper surface power plug/socket connection facility matable with said lower surface power plug/socket connection facility, an upper surface data transmission plug/socket connection facility matable with said lower surface data transmission plug/socket connection facility and an upper surface pneumatic plug/socket connection facility matable with said lower surface pneumatic plug/socket connection facility;
a control unit for controlling the operability of each of said power supply, said data transmission facility and said pneumatic supply; and
end position sensors connected to said supply unit for sending a signal to said control unit when the height-adjustable middle part of the supply unit has been moved upward to an extent indicating that said pins are accommodated by said pin mounts and connections of said power supply, said data transmission facility and said pneumatic supply are in a mated state.

12. A combination in accordance with claim 11, wherein said pneumatic supply provides for the transfer of medical gases as well as the generation of a vacuum.

13. A combination in accordance with claim 11, wherein said end position sensors comprise photoelectric cells.

14. A combination in accordance with claim 11, wherein said medical device is floor supported and one or more of said side surfaces and said upper surface support said medical device in cooperation with said pins support said medical device for lifting as said height-adjustable middle part is moved relative to said ceiling suspended part.

15. A combination in accordance with claim 14, wherein said upper surface comprises plural upper surface portions.

16. A combination in accordance with claim 6, wherein said medical device is floor supported and said medical instrument middle part has a lower surface and said supply unit middle part has an upper surface cooperating said side surfaces for support of said medical device during lifting.

17. A combination in accordance with claim 16, wherein said upper surface comprises plural upper surface portions.

18. A combination in accordance with claim 16, wherein said upper surface power plug/socket connection facility is on one side of said supply unit middle part and said upper surface pneumatic plug/socket connection facility is on another side of said supply unit middle part.

* * * * *